(12) United States Patent
Igarashi et al.

(10) Patent No.: US 8,419,617 B2
(45) Date of Patent: Apr. 16, 2013

(54) APPARATUS FOR INTRODUCTION INTO TEST BODY

(75) Inventors: Takatoshi Igarashi, Nagano (JP); Kazuaki Kojima, Suwa (JP)

(73) Assignee: Olympus Corporation, Tokyo (JP)

( * ) Notice: Subject to any disclaimer, the term of this patent is extended or adjusted under 35 U.S.C. 154(b) by 403 days.

(21) Appl. No.: 12/401,806

(22) Filed: Mar. 11, 2009

(65) Prior Publication Data

US 2009/0240107 A1 Sep. 24, 2009

(30) Foreign Application Priority Data

Mar. 19, 2008 (JP) .................................. 2008-072268

(51) Int. Cl.
*A61B 1/04* (2006.01)
*A61B 1/00* (2006.01)
*A61B 1/06* (2006.01)

(52) U.S. Cl.
USPC ............ 600/109; 600/128; 600/130; 600/160

(58) Field of Classification Search .................. 600/128, 600/130, 171
See application file for complete search history.

(56) References Cited

U.S. PATENT DOCUMENTS

| | | | | |
|---|---|---|---|---|
| 6,495,282 B1 * | 12/2002 | Yoshida et al. | ............... | 429/156 |
| 7,083,579 B2 * | 8/2006 | Yokoi et al. | ................... | 600/593 |
| 7,651,471 B2 * | 1/2010 | Yokoi et al. | ................... | 600/593 |
| 2003/0020810 A1 * | 1/2003 | Takizawa et al. | ............... | 348/68 |
| 2005/0020880 A1 * | 1/2005 | Miyake et al. | ................ | 600/121 |
| 2005/0143624 A1 * | 6/2005 | Iddan | ............................ | 600/112 |
| 2005/0143644 A1 * | 6/2005 | Gilad et al. | ..................... | 600/407 |
| 2006/0004255 A1 * | 1/2006 | Iddan et al. | ..................... | 600/160 |
| 2006/0004257 A1 * | 1/2006 | Gilad et al. | ..................... | 600/160 |
| 2006/0209185 A1 * | 9/2006 | Yokoi | ............................... | 348/65 |
| 2007/0191683 A1 * | 8/2007 | Fujimori | ........................ | 600/173 |
| 2007/0282164 A1 * | 12/2007 | Frisch et al. | .................. | 600/109 |
| 2008/0045789 A1 * | 2/2008 | Sawachi | ........................ | 600/111 |
| 2008/0137891 A1 * | 6/2008 | Vohringer | ..................... | 381/328 |
| 2008/0200757 A1 * | 8/2008 | Glukhovsky et al. | ......... | 600/109 |
| 2009/0198101 A1 * | 8/2009 | Segawa et al. | ................. | 600/109 |
| 2009/0299144 A1 * | 12/2009 | Shigemori et al. | ............. | 600/160 |

FOREIGN PATENT DOCUMENTS

JP 2001-091860 4/2001

\* cited by examiner

*Primary Examiner* — Philip R Smith
*Assistant Examiner* — William Chou
(74) *Attorney, Agent, or Firm* — Scully Scott Murphy & Presser, PC

(57) ABSTRACT

An apparatus for introduction into a test body includes a functional portion for obtaining information on an inside of a test body; a power source for supplying power for driving the functional portion; and an enclosed container for accommodating the functional portion and the power source. A cross-sectional shape orthogonal to a longitudinal direction of the enclosed container is an elliptical shape to make an outer shape small to alleviate a burden on a test subject during introduction into a body by swallowing or the like for test.

10 Claims, 7 Drawing Sheets

APPARATUS FOR INTRODUCTION INTO TEST BODY

This application claims benefit of Japanese Application No. 2008-072268 filed in Japan on Mar. 19, 2008, the contents of which are incorporated by this reference.

BACKGROUND OF THE INVENTION

1. Field of the Invention

The present invention relates to an apparatus for introduction into a test body that is introduced into a test body and obtains information on an inside of the test body.

2. Description of the Related Art

In recent years, a capsule type endoscope equipped with an image pickup function and a wireless communication function has emerged in a field of endoscopes. The capsule type endoscope has a configuration in which during an observation period after the capsule type endoscope is swallowed from a mouth of a test subject, which is a test body, for observation (test) until the capsule type endoscope is naturally excreted from a living body of the test subject, the capsule type endoscope moves inside organs, for example, an esophagus, a stomach, and a small intestine, (in a body cavity), with peristaltic movement of the organs, and sequentially picks up images using the image pickup function.

In an apparatus for introduction into a test body represented by the capsule type endoscope, a battery is often used as a power source for supplying power to a functional portion for obtaining information on an inside of a body. For example, in a capsule type endoscope described in Japanese Patent Application Laid-Open Publication No. 2001-91860, an electrical element holding cylinder, in which an image sensor for forming an image of an object by an objective lens, an image sensor controlling electrical part for controlling the image sensor, and a sending electrical part for wirelessly sending an electrical signal outputted from the image sensor are integrally provided, is included watertight in an exterior case including a transparent cover and a cylindrical cover. In the capsule type endoscope, a button type battery is used as a power source for supplying power to each element. The power is turned on by pressing in a power switch before test, and the capsule type endoscope is swallowed by a test subject and observes an inside of a body of the test subject.

SUMMARY OF THE INVENTION

An apparatus for introduction into a test body according to the present invention includes a functional portion for obtaining information on an inside of a test body; a power source for supplying power for driving the functional portion; and an enclosed container for accommodating the functional portion and the power source, wherein a cross-sectional shape orthogonal to a longitudinal direction of the enclosed container is an elliptical shape. In the apparatus for introduction into a test body according to the present invention, an outer diameter can be reduced in one direction, so that a burden on a test subject can be alleviated during a test in which the apparatus for introduction into a test body is introduced from an oral cavity into a body.

The above and other objects, features and advantages of the invention will become more clearly understood from the following description referring to the accompanying drawings.

DETAILED DESCRIPTION OF PREFERRED EMBODIMENTS

The apparatus for introduction into a test body according to the present invention will be described below with reference to drawings. It should be noted that the drawings used in the following description is schematic, and that a relationship between a thickness and width of each portion, a ratio of a thickness of portions, and the like are different from actual ones. Also, among the drawings, a relationship and ratio of dimensions, and the like may be different.

First Embodiment

Figure 1:
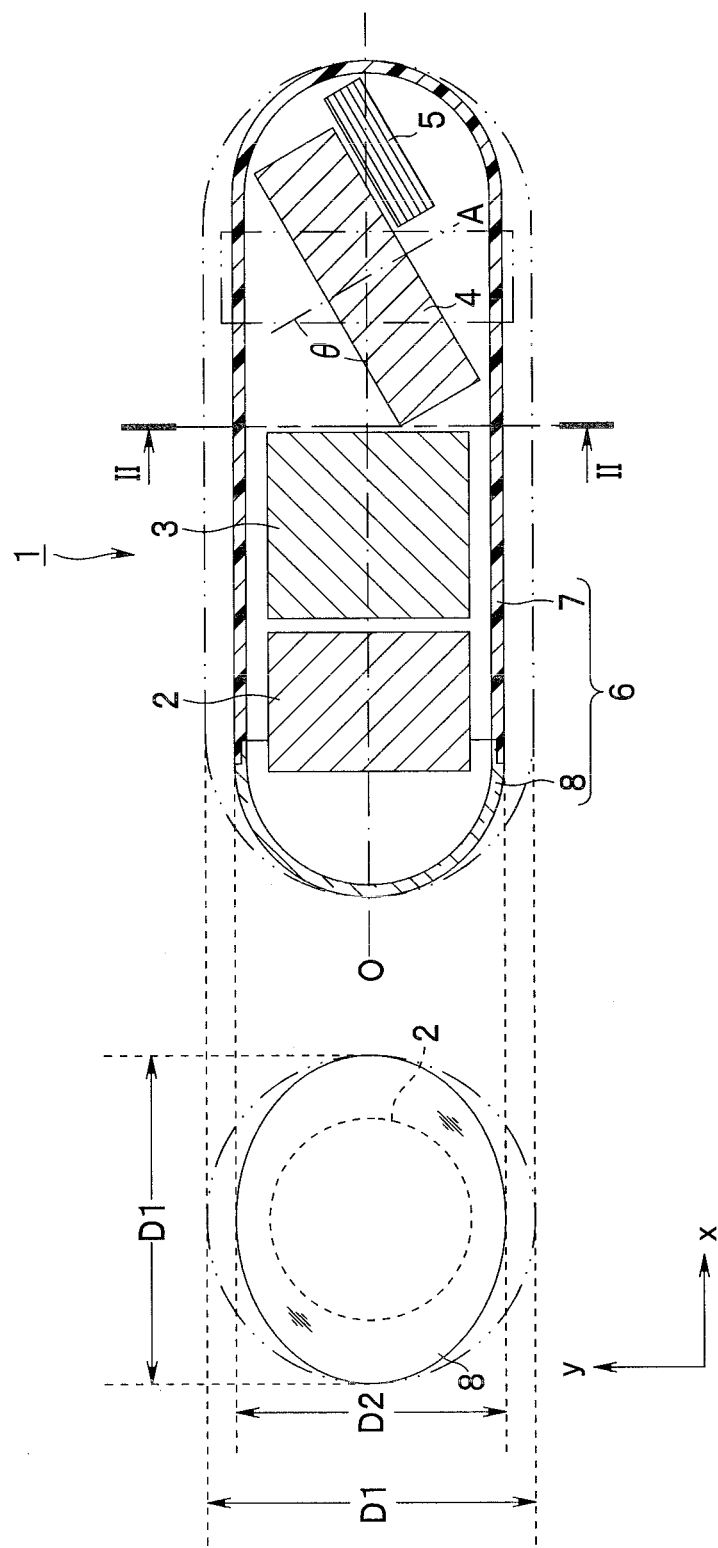
FIG. 1 is a schematic view showing an inner configuration of an apparatus for introduction into a test body according to a first embodiment of the present invention.
Figure 2:
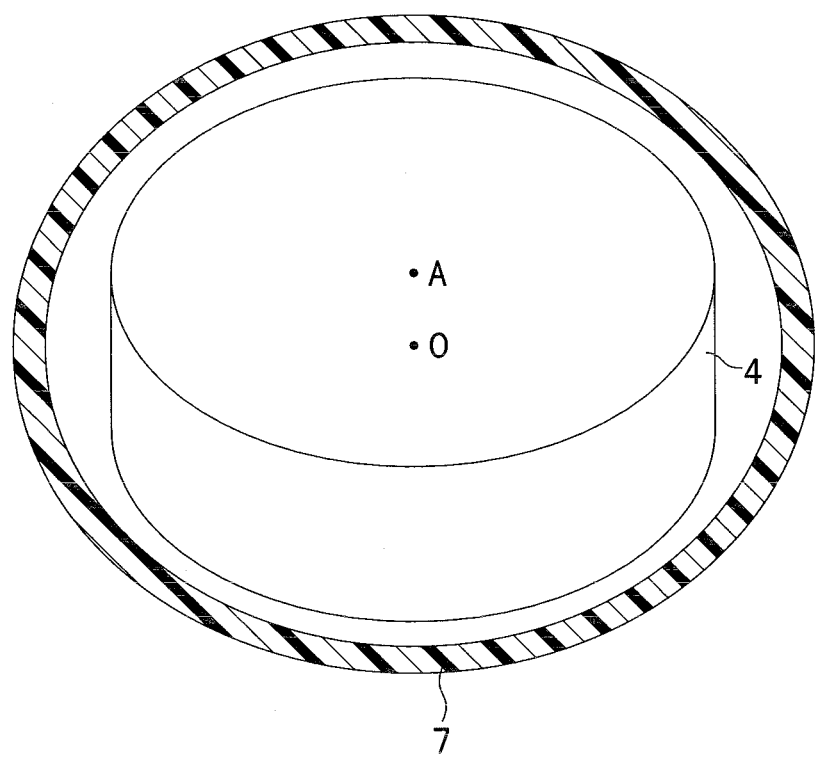
FIG. 2 is a cross-sectional view of the apparatus for introduction into a test body according to the first embodiment, along line II-II in FIG. 1.

First, a first embodiment of the present invention is described with reference to FIG. 1 and FIG. 2. FIG. 1 and FIG. 2 relate to the first embodiment. FIG. 1 is a schematic view showing a configuration of an apparatus for introduction into a test body, and FIG. 2 is a cross-sectional view along line II-II in FIG. 1.

As shown in FIG. 1, in an apparatus for introduction into a test body 1, a sensor unit 2, which is a functional portion for monitoring information on an inside of a test body, a processing circuit system 3, an RF unit 5, and a battery 4, which is a power source, are housed in an exterior case 6, which is an enclosed container. The exterior case 6 is composed of a bottomed cylinder-shaped barrel portion cover 7 and a semielliptical sphere-shaped front portion cover 8, and an inner space is enclosed watertight by the front portion cover 8 being fitted and adhered to block an opening portion of the barrel portion cover 7.

The battery 4 in the present embodiment constitutes a power source of the apparatus for introduction into a test body 1 and is the so-called button type battery, having a generally cylindrical shape, as shown in FIG. 2. The battery 4 is obliquely located in the exterior case 6 of the apparatus for introduction into a test body 1. Also, the RF unit 5 is obliquely located in the exterior case 6 along the obliquely disposed battery 4.

Here, "obliquely located" described above means a non-parallel location state in which a longitudinal central axis O of the barrel portion cover 7 and a transverse central axis A of the cylindrical battery 4 are tilted at a predetermined angle θ.

Also, in the barrel portion cover 7 and the front portion cover 8, a cross-sectional shape in a direction orthogonal to the central axis O of the exterior case 6 is a generally elliptical shape in which a major axis is in an x-axis direction and a minor axis is in a y-axis direction shown in FIG. 1.

When the cylindrical battery 4 is obliquely located in the exterior case 6 in this manner, the cross-sectional shape in the direction orthogonal to the central axis O of the exterior case 6 can be a generally elliptical shape, and a diameter of a main body of the apparatus for introduction into a test body 1 in the y-axis direction can be reduced, compared with a case where the battery 4 is located so that the central axis O of the exterior case 6 and the central axis A of the battery 4 shown by a chain double-dashed line in FIG. 1 are parallel and practically coaxial (hereinafter expressed as the battery 4 being vertically located). In other words, in the exterior case 6 in the present embodiment, a diameter dimension in the y-axis direction can be length D2 smaller than length D1 when the battery 4 is vertically located (D1>D2), as shown in FIG. 1.

Therefore, the apparatus for introduction into a test body 1 can have a smaller diameter, though in one direction. Thus, a burden on a test subject during test can be alleviated. Also, it is considered that the battery 4 is located in the exterior case 6 so that the transverse central axis A is vertical, that is, orthogonal to the central axis O of the exterior case 6, but due to this, a size in a direction of the central axis O, which is a longitudinal direction of the exterior case 6, should be increased. Therefore, the apparatus for introduction into a test body 1 in the present embodiment has a configuration in which the battery 4 is obliquely located so that the transverse central axis A of the battery 4 is at the predetermined angle θ to the central axis O of the exterior case 6, according to a size in the direction of the central axis O, which is the longitudinal direction of the exterior case 6, so as not to impose a burden on a test subject.

The sensor unit 2 may be any sensor that has a function of monitoring information on an inside of a body, such as a pH sensor, a temperature sensor, and an image sensor. When the sensor unit 2 is a pH sensor or a temperature sensor, a part of the sensor unit 2 may be exposed outside the apparatus for introduction into a test body 1 via the front portion cover 8, though not shown. Also, when the sensor unit 2 is an image sensor, which is a solid-state image pickup device, such as a CCD and a CMOS, the front portion cover 8 is preferably light transmissive (transparent).

Information on an inside of a body obtained by the sensor unit 2 is processed by the processing circuit system 3 and sent out of a human body by the RF unit 5 by wireless transmission. Also, the information on the inside of the body sent out of the human body is read by a receiving portion of external equipment not shown.

FIG. 1 illustrates a configuration in which the battery 4 and the RF unit 5 are obliquely located, however, of course, as a configuration for decreasing an outer shape size of the exterior case 6, at least only the battery 4 should be obliquely located, and others should be located to be accommodated in the exterior case 6. Also, FIG. 1 shows a configuration in which the processing circuit system 3 is positioned behind the sensor unit 2, and the battery 4 and the RF unit 5 are arranged in the order behind the processing circuit system 3, however, a positional relationship of portions is not limited to the configuration.

Further, the sensor unit 2, the processing circuit system 3, the RF unit 5, and the battery 4 are electrically connected to each other by respective wirings not shown, such as flexible substrates, for sending and receiving power and signals. It is also possible to provide wiring in clearance between the exterior case 6 and the battery 4 created by obliquely locating the battery 4 in the exterior case 6 as in the present embodiment, and in such a case, flexibility in layout of wiring inside the apparatus for introduction into a test body 1 increases, compared with a case where the battery 4 is vertically located.

As described above, in the apparatus for introduction into a test body 1 in the present embodiment, by obliquely locating the battery 4 so that the transverse central axis A of the battery 4 is at the predetermined angle θ to the longitudinal central axis O of the exterior case 6, the diameter of the main body of the apparatus for introduction into a test body can be reduced, though in one direction. Therefore, particularly, during a test using the apparatus for introduction into a test body 1, which is introduced from an oral cavity of a test subject, a living body, a burden on the test subject can be alleviated. Also, in the apparatus for introduction into a test body 1, a space can be obtained between the battery 4 and the exterior case 6, so that wiring electrically connecting components can be easily provided in an empty space, and flexibility in wiring layout design can be increased.

Second Embodiment

Figure 3:
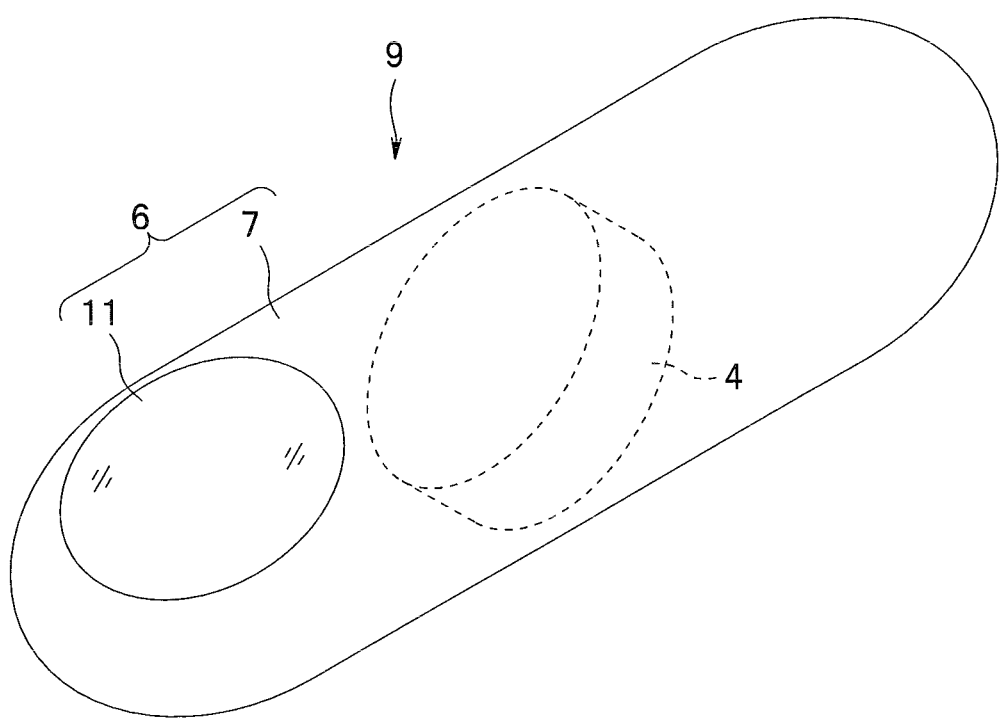
FIG. 3 is a perspective view of an appearance of an apparatus for introduction into a test body according to a second embodiment of the present invention.
Figure 4:
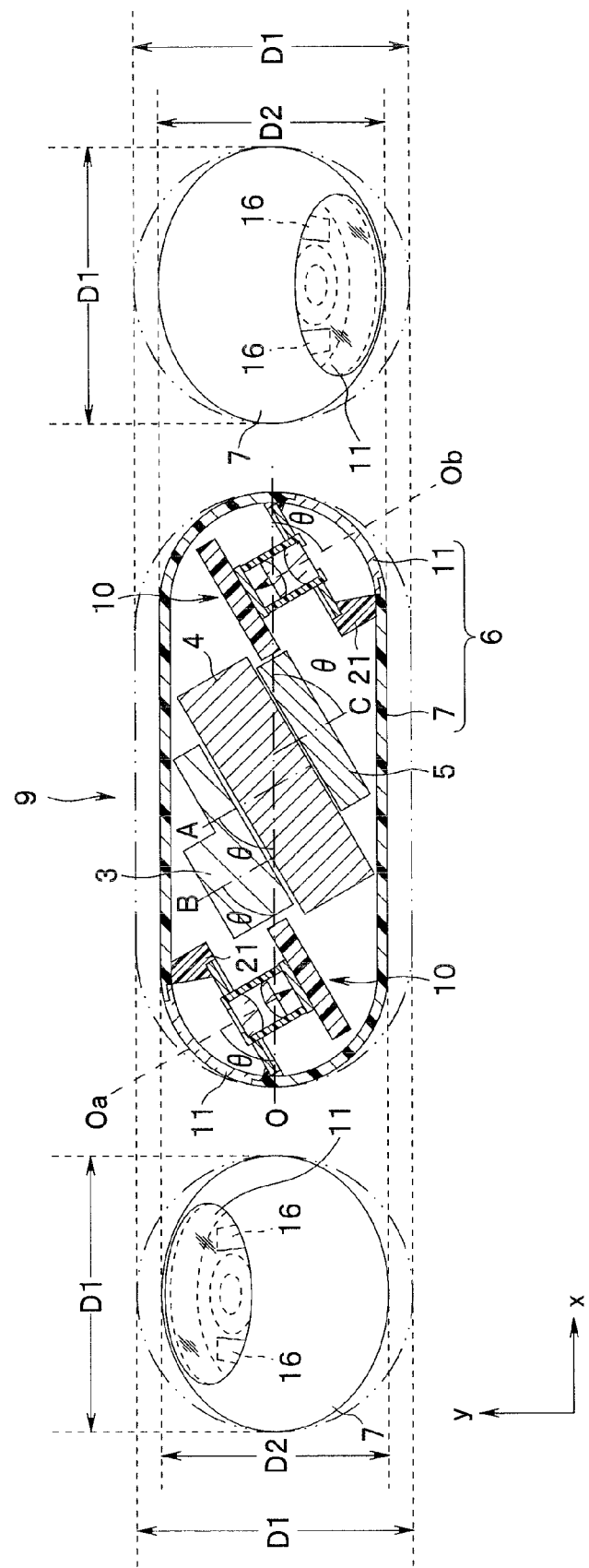
FIG. 4 is a schematic view showing an inner configuration of the apparatus for introduction into a test body according to the second embodiment.
Figure 5:
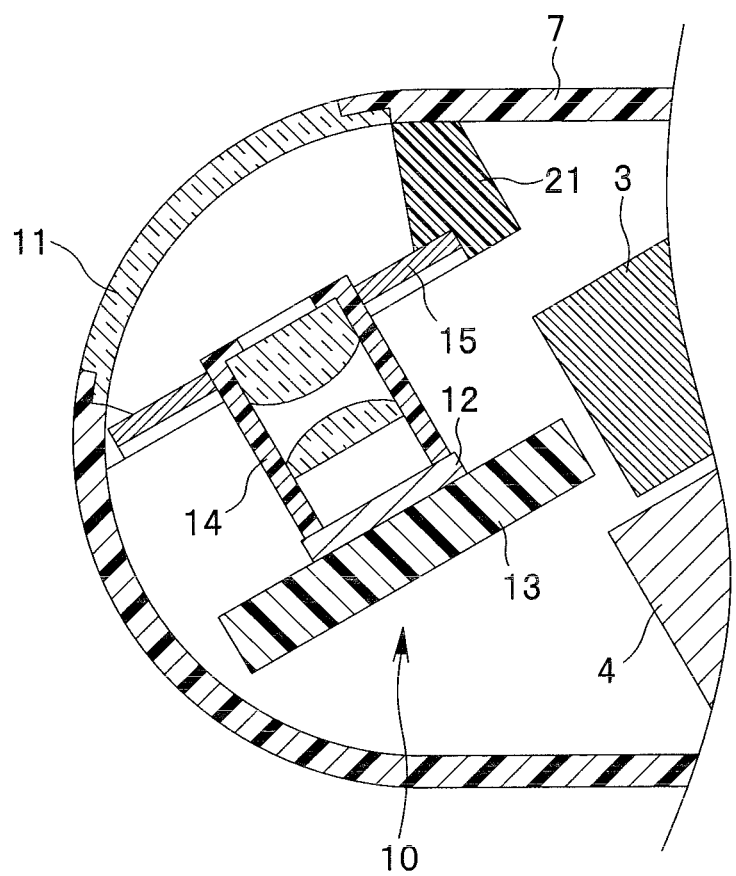
FIG. 5 is an enlarged cross-sectional view for explaining a configuration of an image pickup unit in FIG. 4 according to the second embodiment.
Figure 6:
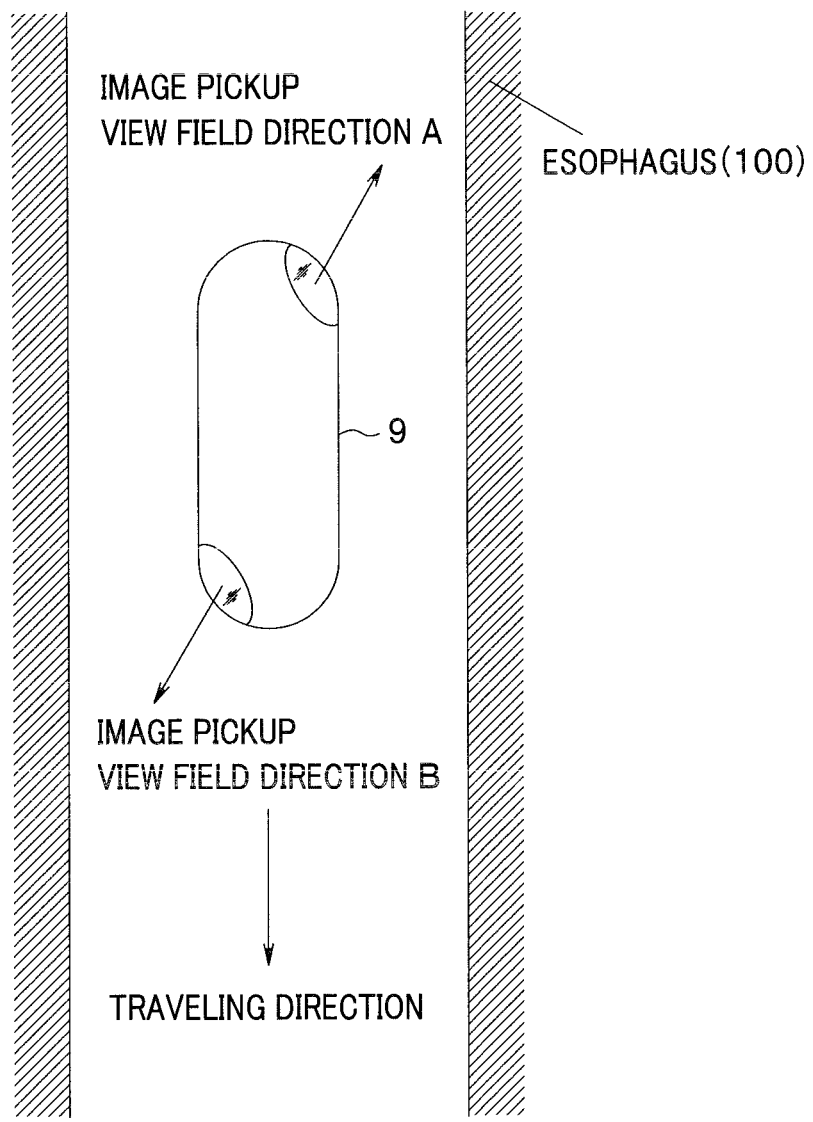
FIG. 6 is a schematic view showing a state in which a capsule type endoscope 9 observes while passing through an esophagus, according to the second embodiment.

Next, a second embodiment of the present invention is described with reference to FIG. 3 to FIG. 6. Also, components common to the first and second embodiments are denoted by the same numerals, and detailed description of the components is omitted. FIG. 3 to FIG. 6 relate to the second embodiment. FIG. 3 is a perspective view of an appearance of an apparatus for introduction into a test body, FIG. 4 is a schematic view showing an inner configuration of the apparatus for introduction into a test body, FIG. 5 is an enlarged cross-sectional view for explaining a configuration of an image pickup unit in FIG. 4, and FIG. 6 is a schematic view showing a state in which a capsule type endoscope 9 observes while passing through an esophagus.

The apparatus for introduction into a test body in the present embodiment shown in FIG. 3 and FIG. 4 is the capsule type endoscope 9 in which images of an inside of a test body can be photographed and obtained in two directions by two image pickup units 10. In the capsule type endoscope 9, the two image pickup units 10, the processing circuit system 3, the RF unit 5, and the battery 4 are housed in the exterior case 6.

Here, all units, the two image pickup units 10, the processing circuit system 3, the RF unit 5, and the battery 4, are obliquely located in the exterior case 6. In other words, in the present embodiment, the processing circuit system 3, the battery 4, and the RF unit 5 are located in the exterior case 6, with respective central axis B (shown by an axis B parallel to a central axis on a sheet of FIG. 4), central axis A, and central axis C tilted at a predetermined angle θ, which is a same angle, to a longitudinal central axis O of the exterior case 6. Also, the two image pickup units 10 are located in the exterior case 6 so that respective photographing optical axes Oa and Ob are tilted at the predetermined angle θ to the longitudinal central axis O of the exterior case 6.

Also, the exterior case 6 in the present embodiment has a generally cylindrical barrel portion cover 7 having hole portions in two places on an upper front side and a lower back side in FIG. 4, and curved surface-shaped light transmissive (transparent) optical domes 11 located to cover the hole portions of the barrel portion cover 7, and an inside is sealed watertight. Also, a cross-sectional shape orthogonal to the longitudinal central axis O of the barrel portion cover 7 is a generally elliptical shape in which a major axis is in an x-axis direction, and a minor axis is in a y-axis direction, as in the first embodiment.

In the two image pickup units 10 disposed inside the exterior case 6, a solid-state image pickup device 12, such as a CCD sensor and a CMOS sensor, is mounted on a wiring substrate 13, such as a rigid substrate and a flexible substrate, as shown in FIG. 5, and the two image pickup units 10 are electrically connected.

In the capsule type endoscope 9 in the present embodiment, light transmitted through each of two optical domes 11 (photographing optical axes Oa and Ob) is collected by a lens unit 14 positioned above a pixel region of the solid-state image pickup device 12 of each image pickup unit 10, and is image-formed in a pixel portion of the solid-state image pickup device 12, so that images of observed sites in two places are obtained.

Also, on an illumination substrate 15 having a generally elliptical plane shape in each image pickup unit 10, a distal end portion of the lens unit 14 is fixed in a center, and LEDs 16 (see FIG. 4), which are illumination means, are mounted on a periphery of the lens unit 14 to sandwich the distal end portion of the lens unit 14, and in a region on a main axis side of an ellipse (the x-axis direction), so that an observed site can be illuminated during observation of an inside of a body cavity. In other words, the image pickup unit 10 is constituted by the solid-state image pickup device 12, the lens unit 14, the LEDs 16, and the wiring substrate 13 and the illumination substrate 15 on which the solid-state image pickup device 12, the lens unit 14, and the LEDs 16 are mounted.

Images obtained by the image pickup units 10 are outputted as image signals by the processing circuit system 3 and wirelessly sent to a receiving portion of external equipment not shown, out of a human body, by the RF unit 5.

Also, the two image pickup units 10 are obliquely located at positions in a front portion and a back portion of the exterior case 6 so that respective image pickup directions are parallel directions at the predetermined angle θ to the longitudinal central axis O of the barrel portion cover 7 and the respective image pickup directions are directions opposite to each other (opposite directions 180° different).

Also, the battery 4 is obliquely located in the exterior case 6 as described above, so that a diameter of a main body of the capsule type endoscope 9 in the y-axis direction is reduced, compared with a case where the battery 4 is located vertically to the longitudinal central axis O of the capsule, that is, the battery 4 is located so that the transverse central axis A is parallel to the longitudinal central axis O of the capsule (accurately on a same axis).

Correspondingly, the processing circuit system 3 and the RF unit 5 are also obliquely located in the exterior case 6 as described above, along the battery 4, so that the diameter of the main body of the capsule type endoscope 9 in the y-axis direction is reduced, compared with a case where the processing circuit system 3 and the RF unit 5 are located vertically to the longitudinal central axis O of the capsule, that is, the processing circuit system 3 and the RF unit 5 are located so that the transverse central axes B and C are parallel to the longitudinal central axis O of the capsule.

In other words, as in the first embodiment, also in the exterior case 6 in the present embodiment, a diameter dimension in the y-axis direction can be length D2 smaller than length D1 when the battery 4 is vertically located (D1>D2), as shown in FIG. 4.

From the above, also in the present embodiment, a burden on a test subject during test can be alleviated, as in the first embodiment. Also, as in the first embodiment, it is possible to provide wiring connecting the image pickup units 10, the processing circuit system 3, the RF unit 5, and the battery 4, in clearance between the exterior case 6 and the battery 4 created by obliquely locating the battery, and in such a case, flexibility in layout of wiring inside the capsule type endoscope 9 increases, compared with a case where the battery 4 is vertically located.

Further, in the present embodiment, the capsule type endoscope 9 includes the two image pickup units 10, so that by sharing components that can be shared among components necessary for signal-processing image pickup signals picked up (photoelectrically converted) by the two image pickup units 10 and wirelessly sending the signal-processed image pickup signals out of a body, the number of parts can be decreased to reduce a manufacturing cost, and an outer shape of the capsule type endoscope 9 can be small.

Here, the twin-lens capsule type endoscope 9 including the two image pickup units 10 is shown as an example, however, of course, a capsule type endoscope having one image pickup unit 10 may also be used.

Next, a state of use of the capsule type endoscope 9, which is the apparatus for introduction into a test body in the present embodiment, is described with reference to FIG. 6.

A power source is turned on before test, and the capsule type endoscope 9 is swallowed by a test subject and introduced into a body cavity. At this time, a burden on the test subject during swallowing is decreased because a diameter of the capsule type endoscope 9 is smaller in one direction. In other words, in the capsule type endoscope 9 in the present embodiment, by obliquely locating the image pickup units 10, the processing circuit system 3, the battery 4, and the RF unit 5 to a longitudinal direction of the exterior case 6, a diameter direction of a main body of the barrel portion cover 7 can be smaller, though one direction, so that a burden on the test subject during test can be alleviated.

Also, when the power source is turned on, the LEDs 16 of each image pickup unit 10 start to light up, and with observed sites illuminated, the two image pickup units 10 pick up a body cavity wall of a test body in two directions. In other words, the capsule type endoscope 9 has the two image pickup units 10, so that in observing a tubular site, such as an esophagus 100, the capsule type endoscope 9 moves in a traveling direction in the figure, which is a direction of a deep portion of a body cavity, while observing an esophagus wall in two directions, an image pickup view field direction A and an image pickup view field direction B.

From the above, in addition to an effect similar to that of the first embodiment, the capsule type endoscope 9 in the present embodiment can photograph obliquely to the traveling direction, and in two directions, directions opposite to each other (180° opposite directions), so that the capsule type endoscope 9 can observe an inside of a body cavity in a wider range than conventional capsule type endoscopes, and diagnosis performance can be improved.

Third Embodiment

Figure 7:
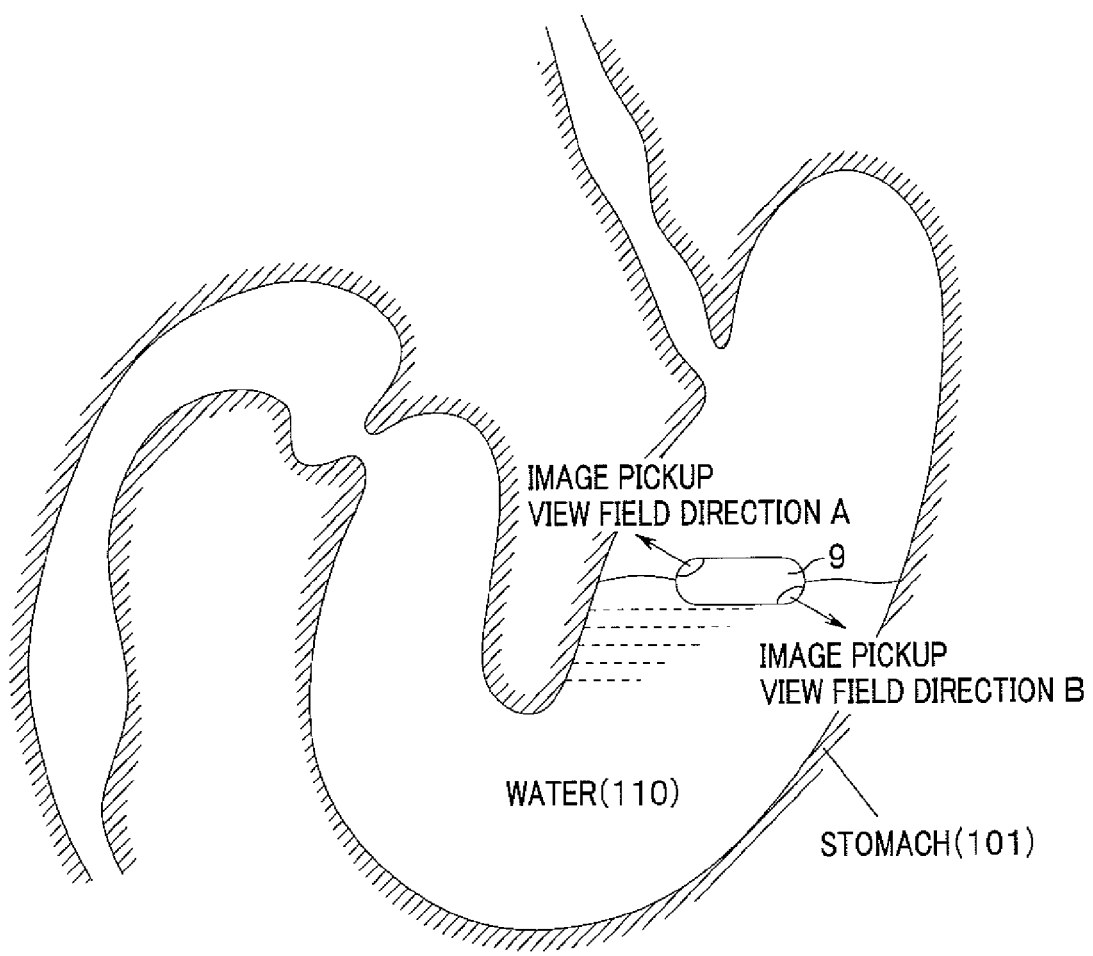
FIG. 7 is a schematic view for explaining an example of use of an apparatus for introduction into a test body according to a third embodiment.

Next, a third embodiment of the present invention is described with reference to FIG. 7. FIG. 7 is a schematic view for explaining an example of use of an apparatus for introduction into a test body according to a third embodiment.

Also, the apparatus for introduction into a test body in the present embodiment is the capsule type endoscope 9 having a configuration similar to that of the second embodiment. In other words, in the capsule type endoscope 9 in the present embodiment, an inner configuration is similar to that of the second embodiment, and the two image pickup units 10, the processing circuit system 3, the battery 4, and the RF unit 5 are included watertight in the exterior case 6.

The two image pickup units 10 are located so that image pickup directions of the two image pickup units 10 are oblique to a longitudinal direction of the capsule and are directions opposite to each other (180° opposite directions), and other processing circuit system 3, battery 4, and RF unit 5 are also all obliquely located.

A weight of each part and a size of the exterior case 6 are designed so that a specific gravity of the capsule type endoscope 9 in the present embodiment is less than 1. The battery 4 is located at a position generally central in a longitudinal direction of the exterior case 6. In other words, the battery 4 accounting for most of a total weight of the capsule type endoscope 9 is located at a generally central position of the exterior case 6. Therefore, a center of gravity of the capsule type endoscope 9 can also be at the generally central position.

After a power source is turned on, the capsule type endoscope 9 is swallowed by a test subject with water 110, and travels while observing an inside of a body cavity. When the capsule type endoscope 9 arrives in a stomach 101, the capsule type endoscope 9 floats in the stomach 101, in which the water 110 is stored in about half a space, and observes the stomach 101.

At this time, the capsule type endoscope 9 can float easily on a surface of the water stored in the stomach 101 because the capsule type endoscope 9 has a specific gravity of less than 1. Also, in the capsule type endoscope 9, a cross-sectional shape orthogonal to the longitudinal direction is an elliptical shape, so that rotation about a longitudinal central axis O does not occur easily, and the center of gravity is positioned at a generally central position of a whole, so that the capsule type endoscope 9 is prevented from leaning toward either one of a front portion and a back portion and being immersed in the water, and a posture of the capsule type endoscope 9 floating on the water surface is stable. In other words, it is easily possible to maintain, for example, a posture such that one image pickup view field direction A is toward an obliquely upper side, and the other image pickup view field direction B is toward an obliquely lower side, which is underwater, as shown in FIG. 6.

From the above, in addition to effects of the above-described embodiments, as a specific effect, the capsule type endoscope 9 in the present embodiment floats in a stable posture on the water surface of the water 110 stored in the stomach 101, so that a surface of the stomach on an underwater side and a side above the water surface can be simultaneously observed by the two image pickup units 10. Thus, the capsule type endoscope 9 in the present embodiment can thoroughly observe an inside of the stomach 101 with few posture changes of the test subject.

The invention described above is not limited to the embodiments, and in the stage of implementation, various modifications can be made without departing from the gist thereof. Further, inventions in various stages are included in the embodiments, and various inventions can be extracted by appropriate combinations of a plurality of components disclosed.

For example, when the effects described are obtained for problems to be solved by the invention even if some components are eliminated from all components shown in the embodiments, a configuration in which the components are eliminated can be extracted as the invention.

What is claimed is:

1. An apparatus for introduction into a test body comprising:
    a functional portion for obtaining information on an inside of a test body;
    a power source for supplying power for driving the functional portion; and
    an elongate shaped enclosed container for accommodating the functional portion and the power source, in which a cross-sectional shape orthogonal to a longitudinal direction is an elliptical shape,
    wherein the power source is a button type battery, and
    wherein the button type battery is located and fixed to the enclosed container so that at least a transverse central axis of the button type battery is oblique at a predetermined angle with respect to a longitudinal central axis of the enclosed container.

2. The apparatus for introduction into a test body according to claim 1, wherein the functional portion is an image pickup unit for picking up an image of an inside of the test body.

3. The apparatus for introduction into a test body according to claim 2, comprising two of the image pickup units in which respective image pickup directions are oblique at a predetermined angle with respect to a longitudinal direction of the enclosed container, and which pick up images in directions opposite to each other.

4. The apparatus for introduction into a test body according to claim 3, wherein a specific gravity of the apparatus is less than 1.

5. The apparatus for introduction into a test body according to claim 4, wherein the button type battery is located so that a center of the button type battery matches a center of the enclosed container.

6. The apparatus for introduction into a test body according to claim 5, wherein the apparatus for introduction into a test body is a capsule type endoscope.

7. The apparatus for introduction into a test body according to claim 4, wherein the apparatus for introduction into a test body is a capsule type endoscope.

8. The apparatus for introduction into a test body according to claim 3, wherein the apparatus for introduction into a test body is a capsule type endoscope.

9. The apparatus for introduction into a test body according to claim 2, wherein the apparatus for introduction into a test body is a capsule type endoscope.

10. The apparatus for introduction into a test body according to claim 1, wherein the apparatus for introduction into a test body is a capsule type endoscope.

* * * * *